US011752277B2

(12) United States Patent
Hua et al.

(10) Patent No.: US 11,752,277 B2
(45) Date of Patent: Sep. 12, 2023

(54) NEBULIZATION DEVICE HAVING DUAL MODULES

(71) Applicant: Jian Hua, Guangdong (CN)

(72) Inventors: Jian Hua, Guangdong (CN); Xuefeng Song, Guangdong (CN)

(73) Assignee: Jian Hua, Guangdong (CN)

( * ) Notice: Subject to any disclaimer, the term of this patent is extended or adjusted under 35 U.S.C. 154(b) by 420 days.

(21) Appl. No.: 15/733,525

(22) PCT Filed: Mar. 13, 2019

(86) PCT No.: PCT/CN2019/078038
§ 371 (c)(1),
(2) Date: Aug. 20, 2020

(87) PCT Pub. No.: WO2020/124814
PCT Pub. Date: Jun. 25, 2020

(65) Prior Publication Data
US 2020/0390984 A1 Dec. 17, 2020

(30) Foreign Application Priority Data
Dec. 19, 2018 (CN) ......................... 201811558686.0
Dec. 19, 2018 (CN) ......................... 201822149015.0

(51) Int. Cl.
*A61M 11/00* (2006.01)
*A61M 16/00* (2006.01)
(Continued)

(52) U.S. Cl.
CPC ............ *A61M 11/00* (2013.01); *A61M 16/00* (2013.01); *A61M 16/06* (2013.01); *A61M 39/08* (2013.01);
(Continued)

(58) Field of Classification Search
CPC ...... A61M 11/00; A61M 16/00; A61M 16/06; A61M 39/08; A61M 2016/0027;
(Continued)

(56) References Cited

U.S. PATENT DOCUMENTS 6,732,731 B1 5/2004 Tseng
2009/0235925 A1 * 9/2009 Power ................. B05B 17/0669 128/200.14
(Continued)

FOREIGN PATENT DOCUMENTS

CN 102727971 A 10/2012
CN 203749970 U 8/2014
(Continued)

OTHER PUBLICATIONS

ISA/CN, PCT International Search Report and Written Opinion dated Aug. 28, 2019 issued in PCT International Application No. PCT/CN2019/078038.

*Primary Examiner* — Rachel T Sippel
(74) *Attorney, Agent, or Firm* — Gottlieb, Rackman & Reisman, PC

(57) ABSTRACT

A nebulization device having dual modules includes: a nebulization host machine; a three-way tube communicated with the nebulization host machine; and a controller connected to the nebulization host machine; the nebulization host machine further includes a side cover, a nozzle arranged on a lower side of the side cover, a liquid medicine bottle arranged on an upper side of the side cover and communicated with the nozzle, a nebulization sheet arranged on one side of the liquid medicine bottle and communicated with the nozzle, and a first plug-in interface arranged below the liquid medicine bottle; a bottom portion within an interior of the nozzle is provided with a partition plate that divides the
(Continued)

interior of the nozzle into an upper nebulization chamber and a lower gas flow chamber.

11 Claims, 5 Drawing Sheets

(51) Int. Cl.
*A61M 16/06* (2006.01)
*A61M 39/08* (2006.01)

(52) U.S. Cl.
CPC ................. *A61M 2016/003* (2013.01); *A61M 2016/0027* (2013.01); *A61M 2205/3331* (2013.01); *A61M 2205/3334* (2013.01); *A61M 2205/3584* (2013.01); *A61M 2205/505* (2013.01); *A61M 2205/587* (2013.01); *A61M 2205/8206* (2013.01); *A61M 2209/08* (2013.01)

(58) Field of Classification Search
CPC .... A61M 2016/003; A61M 2205/3331; A61M 2205/3334; A61M 2205/3584; A61M 2205/505; A61M 2205/587; A61M 2205/8206; A61M 2209/08; G01F 1/684; G01N 2030/8447; G01L 19/147
See application file for complete search history.

(56) References Cited

U.S. PATENT DOCUMENTS

| | | | | |
|---|---|---|---|---|
| 2010/0282247 | A1* | 11/2010 | Kadrichu | A61M 15/0086<br>128/200.14 |
| 2019/0224709 | A1* | 7/2019 | Kelly | B05B 17/0646 |
| 2019/0290879 | A1* | 9/2019 | Kern | A61M 11/005 |
| 2021/0187214 | A1* | 6/2021 | Marcoz | A61M 15/0071 |

FOREIGN PATENT DOCUMENTS

| | | | |
|---|---|---|---|
| CN | 205549165 | U | 9/2016 |
| CN | 106512158 | A | 3/2017 |
| CN | 108371741 | A | 8/2018 |

* cited by examiner

NEBULIZATION DEVICE HAVING DUAL MODULES

CROSS-REFERENCE TO RELATED APPLICATIONS

This application is a national stage filing under 35 U.S.C. § 371 of international application number PCT/CN2019/078038, filed Mar. 13, 2019, which claims priority to Chinese patent application No. 201811558686.0, filed Dec. 19, 2018 and Chinese patent application No. 201822149015.0, filed Dec. 19, 2018. The contents of these applications are incorporated herein by reference in their entirety.

TECHNICAL FIELD

The present invention relates to the field of medical apparatus and instruments, and more particularly, to a nebulization device having dual modules.

BACKGROUND

In modern clinical medicine, a ventilator is used as a device that is able to replace artificial respiration and has an automatic ventilation function, which has been widely used in anesthetic and respiratory management during respiratory failure and major surgery, and respiratory support treatment and emergency resuscitation. The ventilator occupies a very important position in the field of modern medicine, and is commonly found in an ICU ward. The ventilator has a function of supplying and conveying gas, replaces respiratory muscles of a human body to work, is able to generate a certain respiratory rhythm, comprising a respiratory rate and an inspiration and expiration ratio, and has a function of a central nerve of respiration in controlling the respiratory rhythm. Moreover, a proper tidal volume (VT) or a minute ventilation (MV) are provided to meet requirements of respiratory metabolism. Gas supplied by the ventilator is preferably heated and humidified to replace a function of a nasal cavity of the human body, and $O_2$ higher than that contained in the atmosphere is able to be provided, so as to increase a concentration of the inhaled $O_2$ and improve oxygenation. Nebulization inhalation treatment is an important and effective treatment method for a disease of a respiratory system. A nebulizer is used for atomizing a liquid medicine into tiny particles, and then the medicine is inhaled into a respiratory tract by a user through respiration and deposited in a lung, and then absorbed through a mucosa thereof, thus achieving the purpose of painless, rapid and effective treatment. Therefore, it is very important for a specific patient to have a nebulization treatment device capable of being used effectively with the ventilator. However, the nebulization treatment device is unable to actively judge the respiratory rate of the ventilator during use of the existing ventilator. The nebulizer usually sprays at a same rate as the respiratory rate set by the ventilator, which has a high requirement on an operation of the user during actual use, and is prone to an asynchronous phenomenon of nebulization and respiration, thus being very dangerous for the patient. Moreover, the existing nebulizer with a respiration detection function has a defect in a design of a gas passage, which is a problem that it is difficult to detect a weak gas flow. After the nebulizer is used for a long time, the nebulized liquid medicine may generate accumulated water, which easily leads to a defect that electronic components are burned out.

SUMMARY

In view of the above problem, the present invention is intended to provide a nebulization device having dual modules, which is convenient and flexible in use, and is waterproof, and a structure thereof is durable.

In order to achieve the above objective, the present invention provides a nebulization device having dual modules, which comprises a nebulization host machine, a three-way tube communicated with the nebulization host machine, a controller connected to the nebulization host machine, and a ventilator and a mask communicated with the three-way tube respectively. The nebulization host machine comprises a side cover, a nozzle arranged on one side of the side cover, a liquid medicine bottle arranged on the other side of the side cover and communicated with the nozzle, a nebulization sheet arranged on one side of the liquid medicine bottle and communicated with the nozzle, and a first plug-in interface arranged below the liquid medicine bottle. A bottom portion in the nozzle is provided with a partition plate that divides an interior of the nozzle into an upper nebulization chamber and a lower gas flow chamber. The partition plate is provided thereon with a gas flow detection structure extending into an interior of the three-way tube. The gas flow detection structure comprises an inverted trapezoidal plate that is arranged on the bottom portion of the nozzle and integrally connected to the nozzle, and extends into the interior of the three-way tube, a protrusion that is arranged in the interior of the three-way tube and abuts against an end portion of the inverted trapezoidal plate, the lower gas flow chamber that is arranged in an interior of the inverted trapezoidal plate and communicated with the ventilator, and contains a gas flow, a slot arranged in an inner wall of the inverted trapezoidal plate, a sensor arranged in the slot for detecting gas flowing through the lower gas flow chamber, and a first circuit board arranged in the first plug-in interface and connected to the sensor. The nebulization sheet is connected to the first circuit board. The sensor detects a gas flow signal in the lower gas flow chamber, and then sends the signal to the controller, and the controller drives the nebulization host machine to generate a nebulized liquid medicine to be ejected from the nozzle for administration. Therefore, the above structure has two modes during actual use, which are namely that when the sensor is operated, a variable frequency mode is applied, which may actively detect a respiratory state of the ventilator and nebulize the liquid medicine to avoid an asynchronous phenomenon of nebulization and respiration; and when the sensor is not operated, a fixed frequency mode is applied, which may continuously nebulize the liquid medicine without detecting the respiratory state of the ventilator.

In some embodiments, the signal detected by the sensor is a detection signal that the gas flows into the lower gas flow chamber under an expiratory state of the ventilator.

In some embodiments, the sensor is a gas flow sensor or a gas pressure sensor.

In some embodiments, the sensor is wrapped by silica gel and installed in the slot in the inverted trapezoidal plate; and a surface of an electrically connected portion of the sensor facing away from the slot is coated with waterproof glue.

In some embodiments, the three-way tube is connected to the nozzle. A middle port of the three-way tube is connected to the nozzle of the nebulization host machine, and a connection mode thereof is also interference connection. A side wall of the nozzle of the nebulization host machine and the three-way tube are also respectively provided with a clamping groove and a bulge which are mutually engaged for marking a connecting direction, so as to prevent a user from assembling incorrectly.

In some embodiments, the nebulization device having dual modules further comprises a clamp arranged on the controller and fixedly installed on a fence of a sickbed or a table edge. The clamp consists of a buckle for fixedly clamping the controller on one end, and an adjustable clamp for fixing the fence or the table edge on the other end.

In some embodiments, the controller comprises a shell, a key and an indicator light arranged on the shell, a second circuit board arranged in the shell, a battery connected to the second circuit board, and a second plug-in interface arranged on one side of the shell and connected to the second circuit board. The second circuit board comprises a main control module, and a key unit, a nebulization driving module and a power supply circuit which are respectively connected to the main control module. The power supply circuit is respectively connected to the battery and the nebulization driving module. The main control module is connected to the indicator light. The second plug-in interface is connected to the first plug-in interface through a wire.

In some embodiments, the first plug-in interface and the second plug-in interface are detachably connected to form a closed circuit, the first plug-in interface and the second plug-in interface are both provided with a detection metal contact, a circuit negative electrode metal contact, a nebulization positive electrode metal contact and a power supply positive electrode metal contact, the detection metal contact on the first plug-in interface is connected to the sensor, and the detection metal contact on the second plug-in interface is connected to the main control module, which are used for collecting signal output of the sensor. The circuit negative electrode metal contact on the second plug-in interface is connected to the nebulization driving module, and the circuit negative electrode metal contact on the first plug-in interface is respectively connected to the nebulization sheet and the sensor, which are used in a circuit negative electrode shared by the sensor and the nebulization sheet. The nebulization positive electrode metal contact on the second plug-in interface is connected to the nebulization driving module, and the nebulization positive electrode metal contact on the first plug-in interface is connected to the nebulization sheet, which are used for providing an AC voltage required by the nebulization sheet for operation. The power supply positive electrode metal contact on the second plug-in interface is connected to the power supply circuit, and the power supply positive electrode metal contact on the first plug-in interface is connected to the sensor, which are used for providing a DC voltage required by the sensor for operation.

In some embodiments, the controller further comprises a wireless communication module arranged in the main control module for wireless communication with the outside world.

The present invention has the beneficial effects that the device is convenient and flexible in use, and is waterproof, and a structure thereof is durable. Two operation modes are provided, the variable frequency mode may actively detect the respiratory state of the ventilator and nebulize the liquid medicine to avoid the asynchronous phenomenon of nebulization and respiration; and the fixed frequency mode may continuously nebulize the liquid medicine without detecting the respiratory state of the ventilator. That is to say, the respiratory state of the ventilator is judged by detecting the change of the gas flow in a pipeline under the variable frequency mode, when the nebulization host machine detects the gas flow generated in the pipeline of the ventilator in the expiratory state, an electrical signal is sent to a main body of the nebulization device, and the main body of the nebulization device drives the nebulization host machine to nebulize the liquid medicine in the same ventilation pipeline for administration; and when the nebulization host machine detects that the ventilator is in an inspiratory state, the liquid medicine is not nebulized. The present invention not only realizes combination of respiratory treatment and nebulization treatment, and has a better therapeutic effect on a disease; but also avoids the asynchronous phenomenon of nebulization and respiration. The liquid medicine may be continuously nebulized without detecting the respiratory state of the ventilator under the fixed frequency mode, which meets various use needs. In addition, the present invention has a low requirement an operation on a user, and is simple and convenient in use. The nozzle is divided into an independent nebulization chamber and a chamber for detecting the gas flow by the partition plate, so that an operating gas flow of the ventilator may be detected without affecting nebulization, and gas flow detection and nebulization spray are independent of each other, thus meeting various requirements, being simple and convenient in operation, and realizing the purpose of being convenient and flexible in use. Moreover, since the gas chamber is formed by cooperation of the bulge in the three-way tube, the gas flow detection structure of the nozzle and a wall of the three-way tube, and the sensor for detecting the gas flow is arranged inside a front end of the gas flow detection structure of the nozzle, the sensor is completely placed in the gas chamber, so that an interaction area between the sensor and the gas flowing in the gas chamber is larger, and a sensitivity of gas flow detection of the nebulization device is higher. A part of the sensor that may be contacted with water vapor is arranged at the slot below the gas flow detection structure of the nozzle, while a part of the sensor that may not be contacted with water vapor is coated with waterproof glue for waterproof treatment, which may further prevent the sensor from being burned out due to water accumulation of the nebulized liquid medicine. Such unique gas chamber design and waterproof design make the respiration detection more accurate and make the waterproof performance of the electronic components better, thereby realizing the waterproof effect and the durable structure.

DETAILED DESCRIPTION

Figure 1:
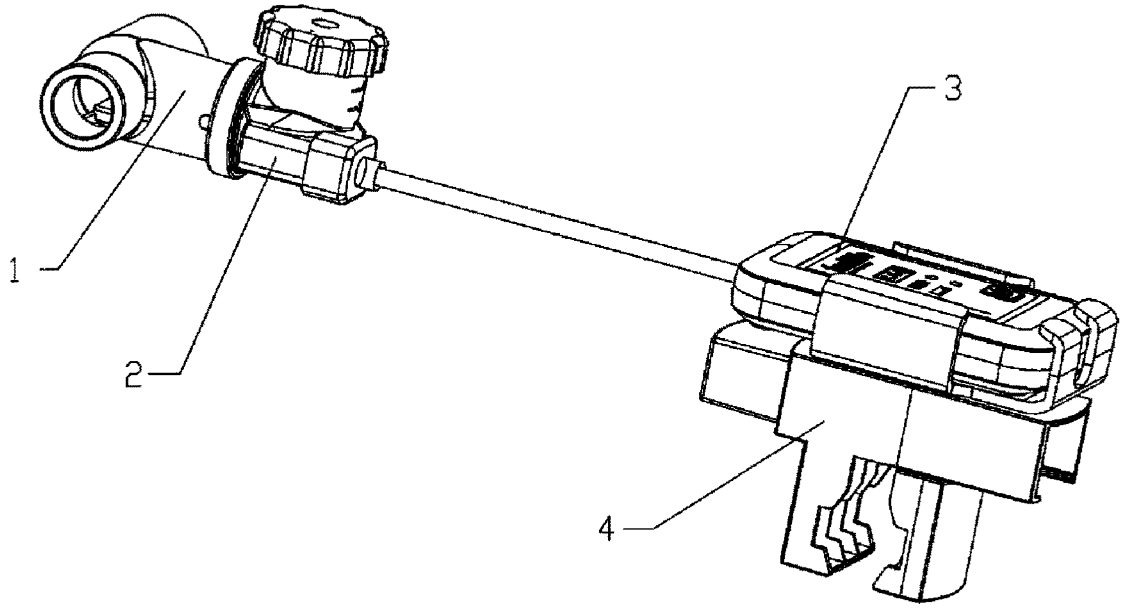
FIG. 1 is a schematic structure diagram of the present invention.
Figure 2:
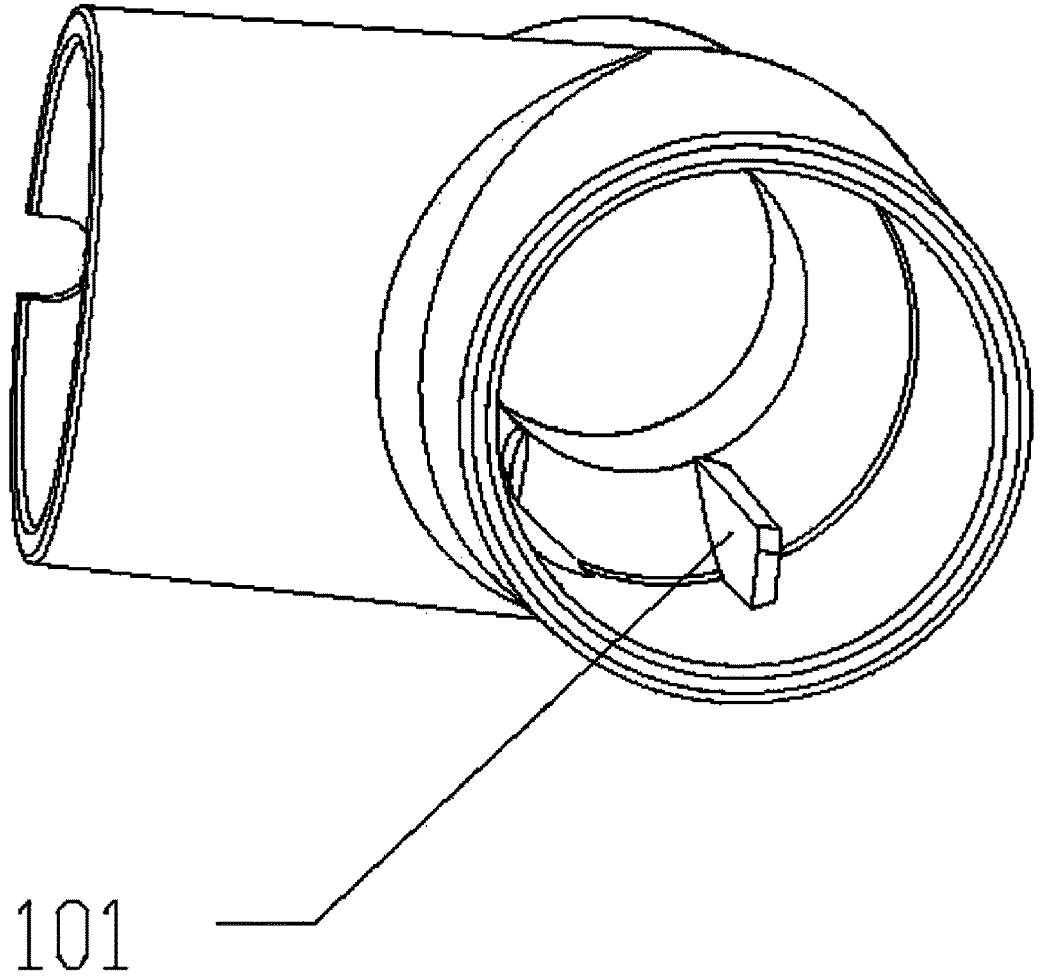
FIG. 2 is a schematic structure diagram of a three-way tube.
Figure 3:
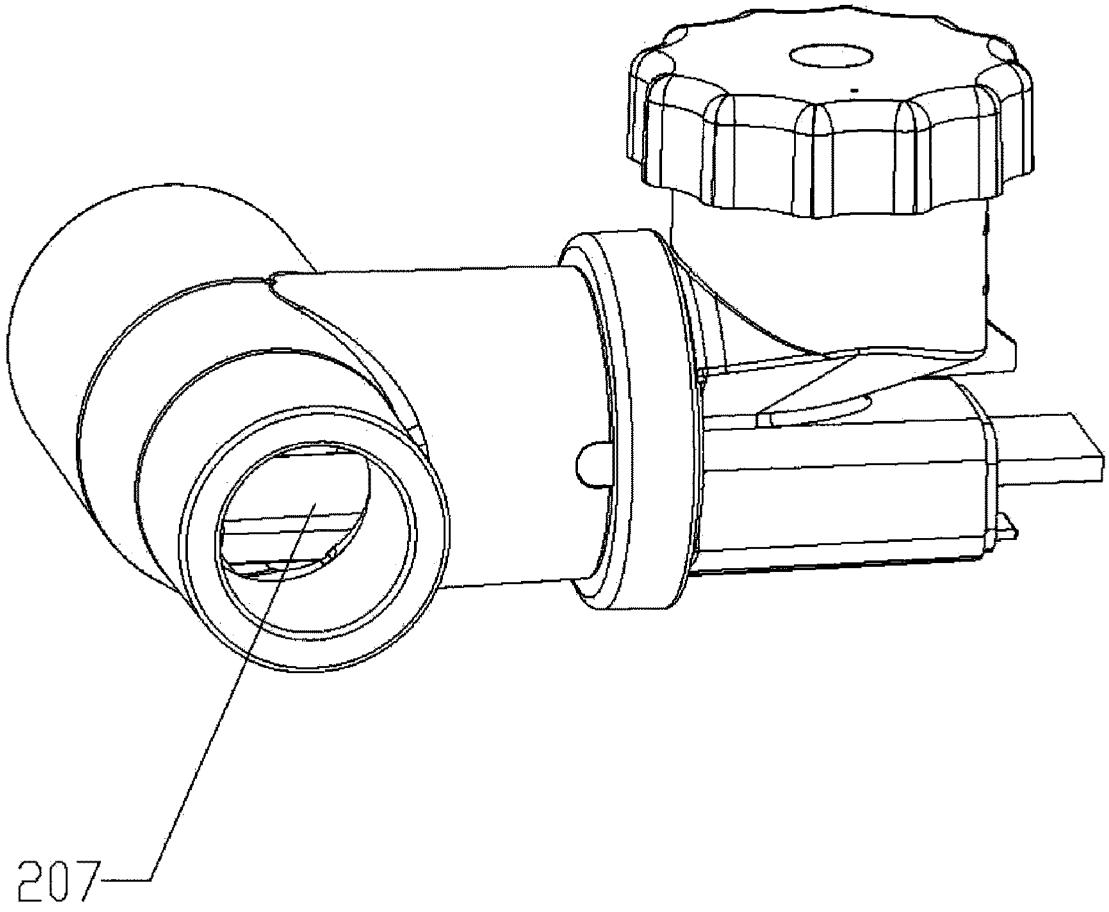
FIG. 3 is a schematic structure diagram of a three-way tube and a nebulization host machine.
Figure 4:
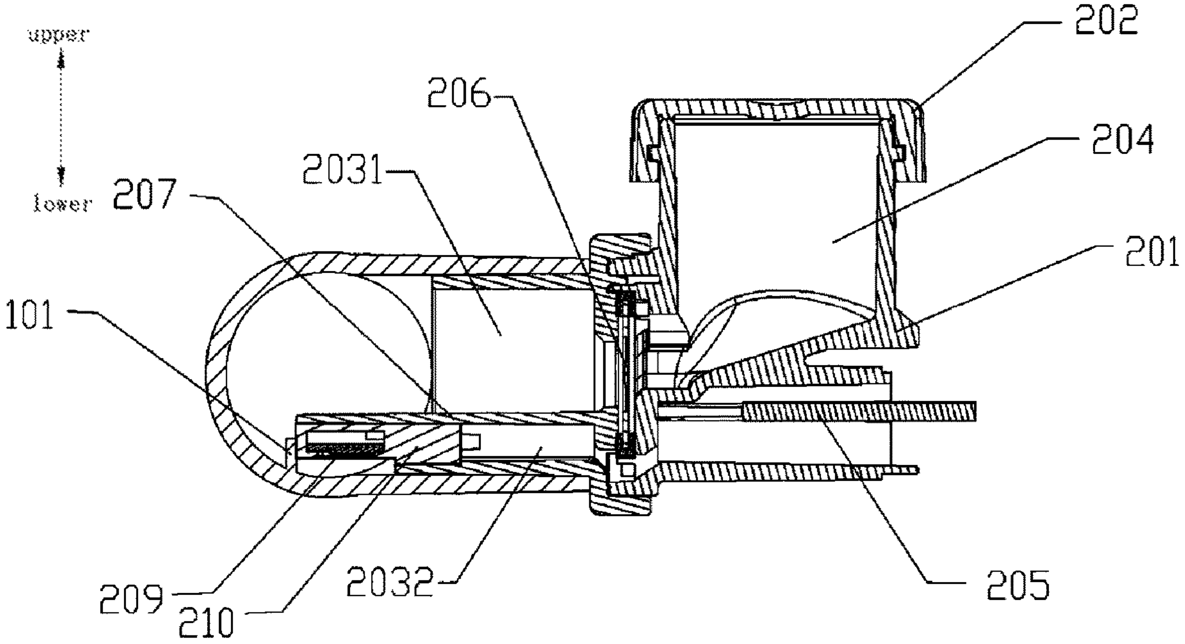
FIG. 4 is a schematic structure diagram of a cross-section of a three-way tube connected to a nebulization host machine.
Figure 5:
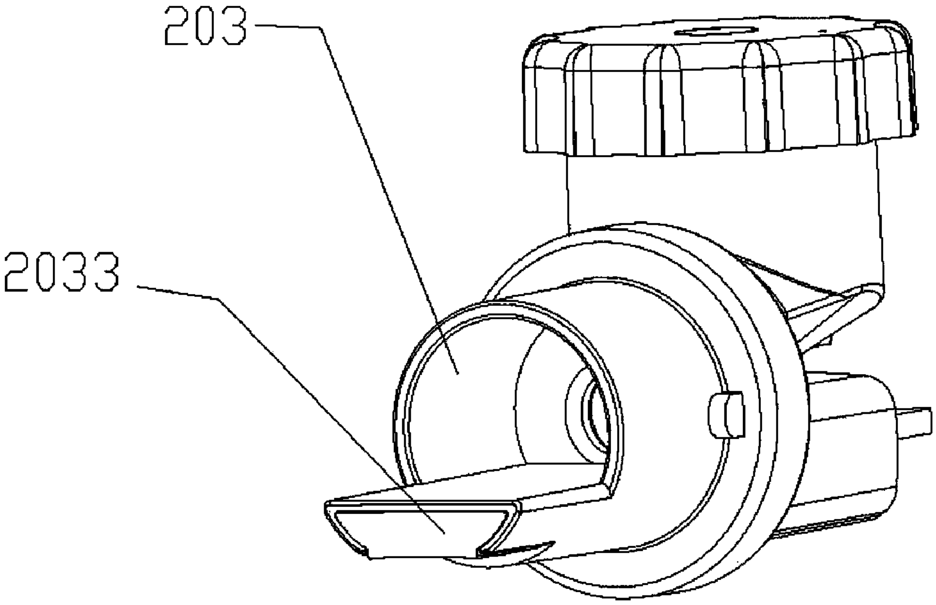
FIG. 5 is a schematic structure diagram of a nebulization host machine.
Figure 6:
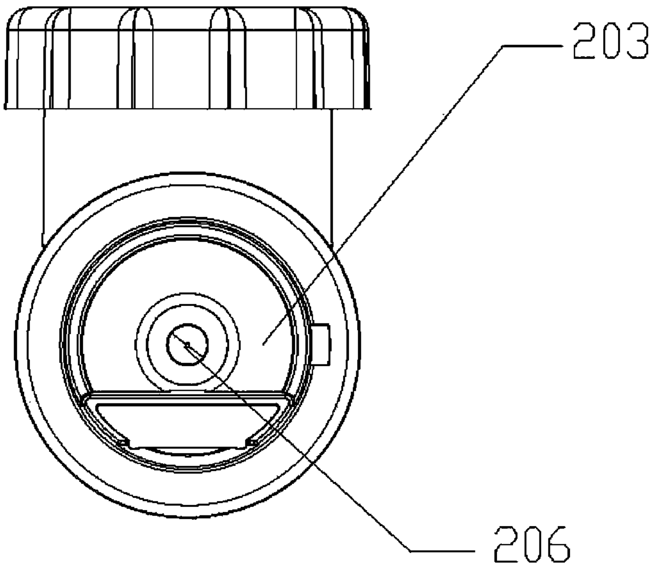
FIG. 6 is a schematic structure diagram of a front view of a nebulization host machine.
Figure 7:
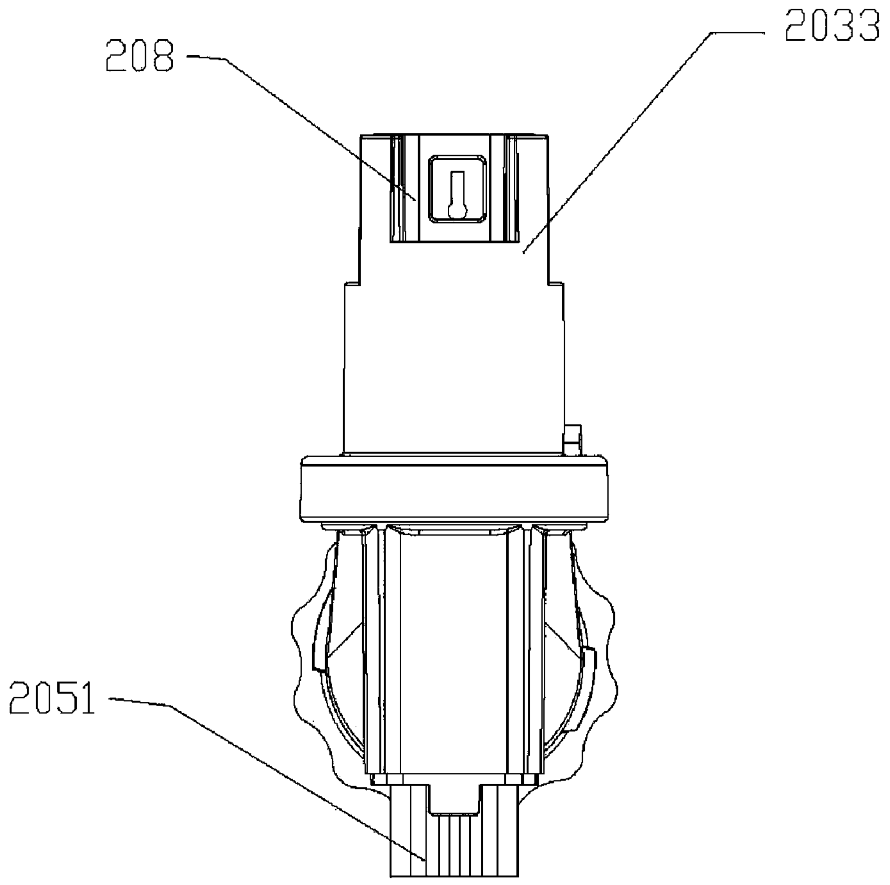
FIG. 7 is a schematic structure diagram of a bottom view of a nebulization host machine.
Figure 8:
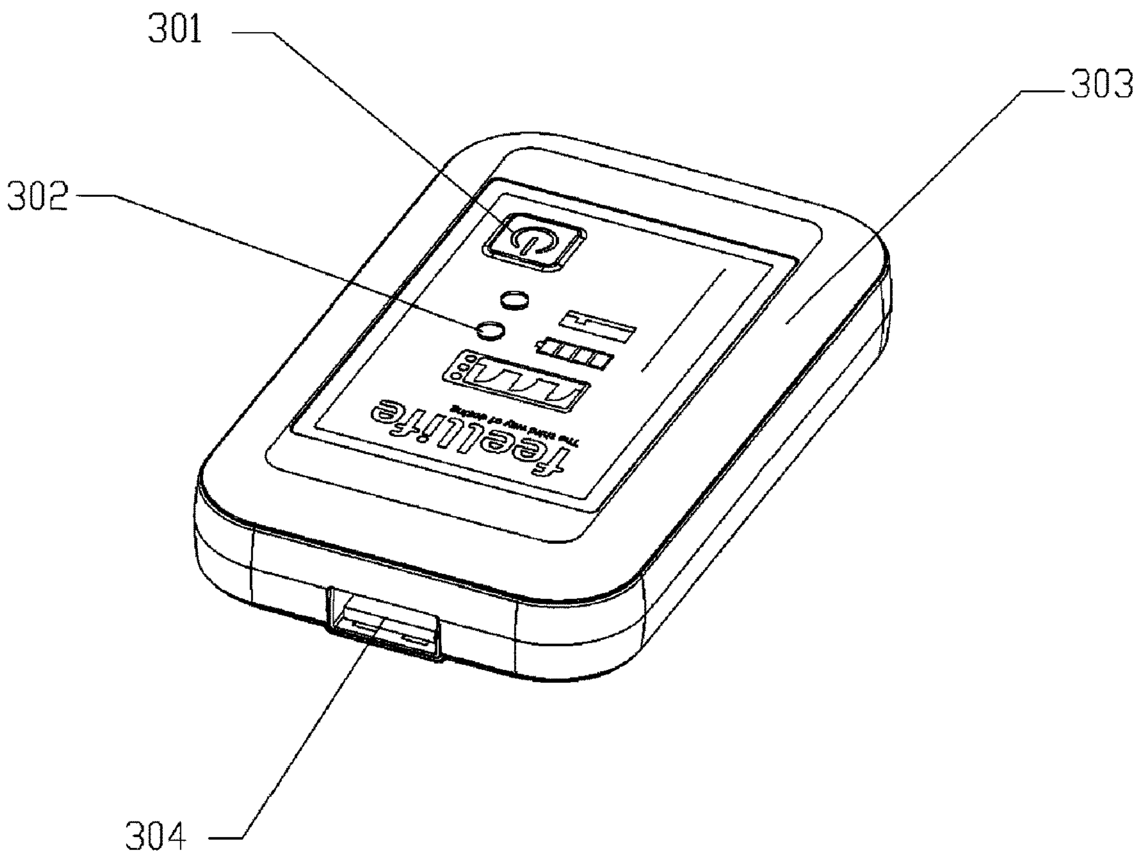
FIG. 8 is a schematic structure diagram of a controller.

The present invention is further described in detail hereinafter with reference to the accompanying drawings.

As shown in FIG. 1 to FIG. 8, a nebulization device having dual modules comprises a nebulization host machine 2, a three-way tube 1 communicated with the nebulization host machine 2, a controller 3 connected to the nebulization host machine 2, and a ventilator and a mask communicated with the three-way tube 1 respectively. The ventilator and the mask above may be connected to the three-way tube 1 in a close-fitting manner, so that a connection structure is simpler. Openings at left and right ends of the three-way tube 1 have different diameters to distinguish different ports connected to the ventilator and the mask. The nebulization device having dual modules further comprises a clamp 4 arranged on the controller 3 and fixedly installed on a fence of a sickbed or a table edge. The clamp 4 consists of a buckle for fixedly clamping the controller 3 on one end, and an adjustable clamp for fixing the fence or the table edge on the other end. The controller 3 further comprises a wireless communication module arranged in the main control module for wireless communication with the outside world. Wi-Fi and/or Bluetooth may be used as the wireless communication module. In some modified embodiments, the controller 3 further comprises a display screen connected to the main control unit for displaying a nebulization parameter and a life parameter of a user. A touch screen may also be used as the display screen instead of a mechanical key to further improve interactive experience. The nebulization host machine 2 comprises a side cover 201, a nozzle 203 arranged on one side of the side cover 201, a liquid medicine bottle 204 arranged on the other side of the side cover 201 and communicated with the nozzle 203, a nebulization sheet 206 arranged on one side of the liquid medicine bottle 204 and communicated with the nozzle, and a first plug-in interface 2051 arranged below the liquid medicine bottle 204. The liquid medicine bottle 204 is provided with an upper cover 202. A bottom portion in the nozzle 203 is provided with a partition plate 207 that divides an interior of the nozzle 203 into an upper nebulization chamber 2031 and a lower gas flow chamber 2032. The partition plate 207 is provided thereon with a gas flow detection structure 2033 extending into an interior of the three-way tube 1. The gas flow detection structure 2033 comprises an inverted trapezoidal plate that is arranged on the bottom portion of the nozzle 203 and integrally connected to the nozzle 203, and extends into the interior of the three-way tube 1, a protrusion 101 that is arranged in the interior of the three-way tube 1 and abuts against an end portion of the inverted trapezoidal plate, the lower gas flow chamber that is arranged in an interior of the inverted trapezoidal plate and communicated with the ventilator, and contains a gas flow, a slot 208 arranged in an inner wall of the inverted trapezoidal plate, a sensor 209 arranged in the slot 208 for detecting gas flowing through the lower gas flow chamber, and a first circuit board 205 arranged in the first plug-in interface 2051 and connected to the sensor 209. The nebulization sheet 206 is connected to the first circuit board 205. The above sensor 209 is completely placed in the lower gas flow chamber, so that an interaction area between the sensor 209 and the gas flowing in the lower gas flow chamber is larger, and a sensitivity of gas flow detection of the nebulization device is higher. Logic control, power supply and interaction of the portable nebulizer are all concentrated on the controller 3. The sensor 209 detects a gas flow signal in the lower gas flow chamber, and then sends the signal to the controller 3, and the controller 3 drives the nebulization host machine 2 to generate a nebulized liquid medicine to be ejected from the nozzle 203 for administration. The signal detected by the sensor 209 is a detection signal that the gas flows into the lower gas flow chamber under an expiratory state of the ventilator. The sensor 209 is a gas flow sensor or a gas pressure sensor. The sensor 209 is wrapped by silica gel 210 and installed in the slot 208 in the inverted trapezoidal plate. A surface of an electrically connected portion of the sensor 209 facing away from the slot 208 is coated with waterproof glue, so as to further prevent the sensor 209 from being burned out due to water accumulation of the nebulized liquid medicine. The three-way tube 1 is connected to the nozzle 203. A middle port of the three-way tube 1 is connected to the nozzle 203 of the nebulization host machine 2, and a connection mode thereof is also interference connection. A side wall of the nozzle 203 of the nebulization host machine 2 and the three-way tube 1 are also respectively provided with a clamping groove and a bulge which are mutually engaged for marking a connecting direction, so as to prevent a user from assembling incorrectly. The controller 3 comprises a shell 303, a key 301 and an indicator light 302 arranged on the shell 303, a second circuit board arranged in the shell 303, a battery connected to the second circuit board, and a second plug-in interface 304 arranged on one side of the shell 303 and connected to the second circuit board. The second circuit board comprises a main control module, and a key unit, a nebulization driving module and a power supply circuit which are respectively connected to the main control module. The power supply circuit is respectively connected to the battery and the nebulization driving module. The main control module is connected to the indicator light. The second plug-in interface 304 is connected to the first plug-in interface 2051 through a wire. The power supply circuit comprises a DC and AC conversion circuit and a boosted circuit, which provide an AC voltage and a DC voltage required by the nebulization sheet 206 and the sensor 209 respectively. In some modified embodiments, the power supply circuit further comprises a charging circuit and a power supply switching circuit, which may charge the battery and switch to external power supply when connected to an external AC voltage. The first plug-in interface 2051 and the second plug-in interface 304 are detachably connected to form a closed circuit, and the first plug-in interface 2051 and the second plug-in interface 304 are both provided with a detection metal contact, a circuit negative electrode metal contact, a nebulization positive electrode metal contact and a power supply positive electrode metal contact. The detection metal contact on the first plug-in interface 2051 is connected to the sensor 209, and the detection metal contact on the second plug-in interface 304 is connected to the main control module, which are used for collecting signal output of the sensor 209. The circuit negative electrode metal contact on the second plug-in interface 304 is connected to the nebulization driving module, and the circuit negative electrode metal contact on the first plug-in interface 2051 is respectively connected to the nebulization sheet 206 and the sensor 209, which are used in a circuit negative electrode shared by the sensor 209 and the nebulization sheet 26. The nebulization positive electrode metal contact on the second plug-in interface 304 is connected to the nebulization driving module, and the nebulization positive electrode metal contact on the first plug-in interface 2051 is connected to the nebulization sheet 206, which are used for providing an AC voltage required by the nebulization sheet 206 for operation. The power supply positive electrode metal contact on the second plug-in interface 304 is connected to the power supply circuit, and the power supply positive electrode metal contact on the first plug-in interface

2051 is connected to the sensor 209, which are used for providing a DC voltage required by the sensor 209 for operation.

Figure 9:
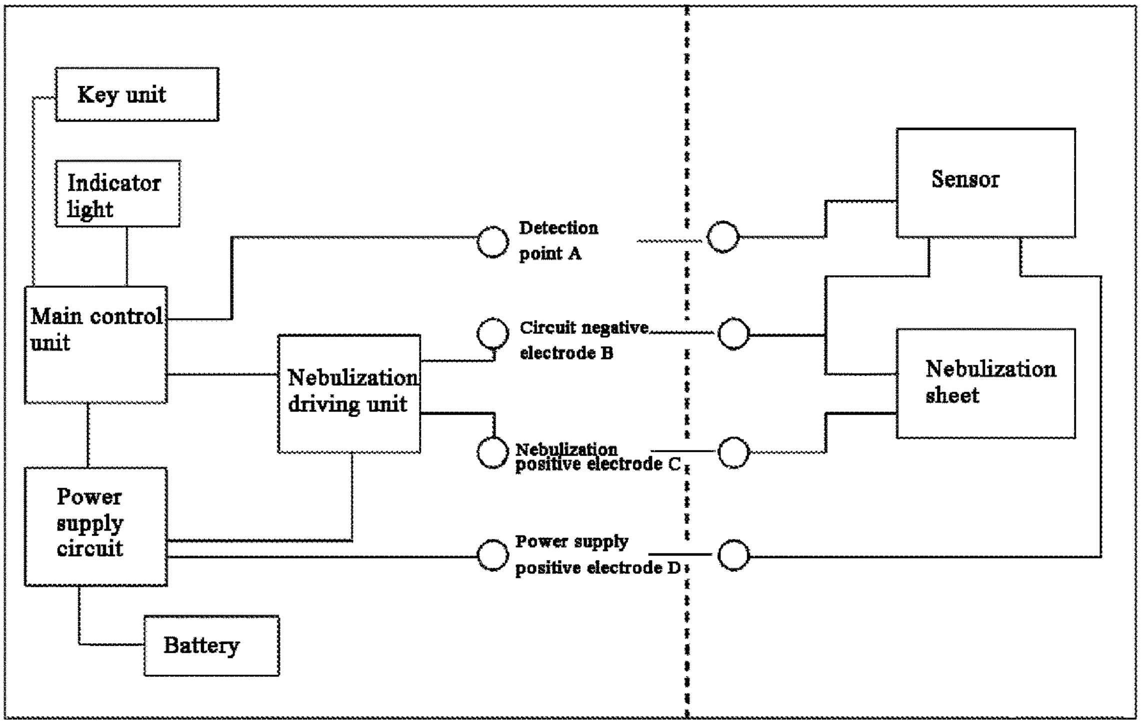
FIG. 9 is a block principle diagram of a circuit of the present invention.

As shown in FIG. 9, the first plug-in interface 2051 and the second plug-in interface 304 are respectively provided with four metal contacts, which are namely a detection point A, a circuit negative electrode B, a nebulization positive electrode C and a power supply positive electrode D in sequence, and the detection point A is respectively connected to the sensor 209 and the main control unit, and is used for collecting the signal output of the sensor 209. The circuit negative electrode B is respectively connected to the nebulization driving unit, the nebulization sheet 206 and the sensor 209, and is used in the circuit negative electrode shared by the sensor 209 and the nebulization sheet 206. The nebulization positive electrode C is respectively connected to the nebulization driving unit and the atomizing sheet 206, and is used for providing the AC voltage required by the nebulization sheet 206 for operation. The power supply positive electrode D is respectively connected to the power supply circuit and the sensor 209, and is used for providing the DC voltage required by the sensor 209 for operation. In the embodiment, the nebulization device further comprises connecting wires which are detachably and electrically connected to the first plug-in interface 2051 of the nebulization host machine 2 and the second plug-in interface 304 of the controller 3 respectively.

Operation principle: a respiratory state of the ventilator is judged by detecting a change of a gas flow in a pipeline under a variable frequency mode, when the nebulization host machine 2 detects the gas flow generated in the pipeline of the ventilator in the expiratory state, an electrical signal is sent to the controller 3, and the controller 3 drives the nebulization host machine 2 to nebulize the liquid medicine in the same ventilation pipeline for administration. When the nebulization host machine 2 detects that the ventilator is in the expiratory state, the liquid medicine is not nebulized. However, the liquid medicine may be continuously nebulized without detecting the respiratory state of the ventilator under a fixed frequency mode. Moreover, the sensor 209 for detecting the gas flowing in the lower gas flow chamber may be a gas flow sensor or a gas pressure sensor. The difference is that the gas pressure sensor may detect a gas pressure. When the sensor 209 of the nebulization host machine 2 detects the gas flow, a corresponding electrical signal is sent to the controller 3. A positive number read by the main control unit indicates a positive gas pressure in a gas pipeline, which means that the ventilator is in the expiratory state at the moment. Meanwhile, the nebulization host machine 2 is driven to nebulize, and the nebulized liquid medicine will enter a mouth of a patient together with the gas supplied by the ventilator through an opening of the three-way tube 1 and the mask. On the contrary, a negative number read by the main control unit indicates a negative gas pressure in the gas pipeline, which means that the ventilator is in an inspiratory state at the moment, and the main control unit should control the nebulization host machine 2 to stop atomizing at the moment. Moreover, the gas flow sensor 209 may detect an instantaneous flow rate and a direction of the gas. The positive and negative data read by the main control unit indicates different flowing directions of the gas. For example, the positive number may indicate that the gas flows from an opening of the ventilator to the interior of the three-way tube 1, which means that the ventilator is in the expiratory state at the moment; and the negative number indicates that the gas flows from the interior of the three-way tube 1 to the opening of the ventilator, which means that the ventilator is in the inspiratory state at the moment, and whether the nebulization host machine 2 sprays in different states of the ventilator is consistent with the gas pressure sensor 209.

The above embodiments are some embodiments of the present invention. Those of ordinary skills in the art may further make several modifications and improvements without departing from the inventive concept of the present invention, and these modifications and improvements all fall within the scope of protection of the present invention.

The invention claimed is:

1. A nebulization device having dual modules, comprising:

a nebulization host machine;

a three-way tube communicated with the nebulization host machine; and a controller connected to the nebulization host machine, wherein:

the nebulization host machine comprises a side cover, a nozzle arranged on a lower side of the side cover, a liquid medicine bottle arranged on an upper side of the side cover and communicated with the nozzle, a nebulization sheet arranged on one side of the liquid medicine bottle and communicated with the nozzle, and a first plug-in interface arranged below the liquid medicine bottle;

a bottom portion within an interior of the nozzle is provided with a partition plate that divides the interior of the nozzle into an upper nebulization chamber and a lower gas flow chamber;

the partition plate is provided thereon with a gas flow detection structure extending into an interior of the three-way tube;

the gas flow detection structure comprises an inverted trapezoidal plate that is arranged on the bottom portion of the nozzle and integrally connected to the nozzle, and extends into the interior of the three-way tube, a protrusion that is arranged in the interior of the three-way tube and abuts against an end portion of the inverted trapezoidal plate, the lower gas flow chamber that is arranged in an interior of the inverted trapezoidal plate and contains a gas flow, a slot arranged in an inner wall of the inverted trapezoidal plate, a sensor arranged in the slot for detecting gas flowing through the lower gas flow chamber, and a first circuit board arranged in the first plug-in interface and connected to the sensor;

the nebulization sheet is connected to the first circuit board; and the sensor detects a gas flow signal in the lower gas flow chamber, and then sends the gas flow signal to the controller, and the controller drives the nebulization host machine to generate a nebulized liquid medicine to be ejected from the nozzle for administration.

2. The nebulization device having dual modules of claim 1, wherein the gas flow signal detected by the sensor is a detection signal that the gas flow flows into the lower gas flow chamber.

3. The nebulization device having dual modules of claim 2, wherein the sensor is a gas flow sensor or a gas pressure sensor.

4. The nebulization device having dual modules of claim 1, wherein the sensor is wrapped by silica gel and installed in the slot in the inverted trapezoidal plate; and a surface of an electrically connected portion of the sensor facing away from the slot is coated with waterproof glue.

5. The nebulization device having dual modules of claim 1, wherein the three-way tube is connected to the nozzle.

6. The nebulization device having dual modules of claim 1, further comprising a clamp arranged on the controller, and the clamp is fixedly installed on a fence of a sickbed or a table edge, wherein:

the clamp consists of a buckle for fixedly clamping the controller located on a first end of the clamp which is close to the controller, and an adjustable clamp for fixing the fence or the table edge located on a second end of the clamp which is close to the fence or the table edge.

7. The nebulization device having dual modules of claim 1, wherein the controller comprises a shell, a key and an indicator light arranged on the shell, a second circuit board arranged in the shell, a battery connected to the second circuit board, and a second plug-in interface arranged on one side of the shell and connected to the second circuit board;

the second circuit board comprises a main control module, a key unit, a nebulization driving module and a power supply circuit, wherein the key unit, the nebulization driving module and the power supply circuit are respectively connected to the main control module;

the power supply circuit is respectively connected to the battery and the nebulization driving module; and the main control module is connected to the indicator light; and the second plug-in interface is connected to the first plug-in interface through a wire.

8. The nebulization device having dual modules of claim 7, wherein the first plug-in interface and the second plug-in interface are detachably connected to form a closed circuit; the first plug-in interface and the second plug-in interface are both provided with a detection metal contact, a circuit negative electrode metal contact, a nebulization positive electrode metal contact and a power supply positive electrode metal contact; the detection metal contact on the first plug-in interface is connected to the sensor, and the detection metal contact on the second plug-in interface is connected to the main control module, which are used for collecting signal output of the sensor; the circuit negative electrode metal contact on the second plug-in interface is connected to the nebulization driving module, and the circuit negative electrode metal contact on the first plug-in interface is respectively connected to the nebulization sheet and the sensor, which are used in a circuit negative electrode shared by the sensor and the nebulization sheet; the nebulization positive electrode metal contact on the second plug-in interface is connected to the nebulization driving module, and the nebulization positive electrode metal contact on the first plug-in interface is connected to the nebulization sheet, which are used for providing an AC voltage required by the nebulization sheet for operation; and the power supply positive electrode metal contact on the second plug-in interface is connected to the power supply circuit, and the power supply positive electrode metal contact on the first plug-in interface is connected to the sensor, which are used for providing a DC voltage required by the sensor for operation.

9. The nebulization device having dual modules of claim 7, wherein the controller further comprises a wireless communication module arranged in the main control module for wireless communication.

10. The nebulization device having dual modules of claim 2, wherein the sensor is wrapped by silica gel and installed in the slot in the inverted trapezoidal plate; and a surface of an electrically connected portion of the sensor facing away from the slot is coated with waterproof glue.

11. The nebulization device having dual modules of claim 3, wherein the sensor is wrapped by silica gel and installed in the slot in the inverted trapezoidal plate; and a surface of an electrically connected portion of the sensor facing away from the slot is coated with waterproof glue.

* * * * *